US009037212B2

(12) United States Patent
Sanjay-Gopal et al.

(10) Patent No.: US 9,037,212 B2
(45) Date of Patent: May 19, 2015

(54) ENABLEMENT OF QUICK REMOTE ACCESS TO CT SCANS TO IMPROVE WORKFLOW AND PATIENT THROUGHPUT

(75) Inventors: Sethumadavan Sanjay-Gopal, Mayfield, OH (US); Scott Kenneth Pohlman, Willoughby, OH (US); Jacob Scott Durgan, Mayfield Heights, OH (US)

(73) Assignee: Koninklijke Philips N.V., Eindhoven (NO)

( * ) Notice: Subject to any disclaimer, the term of this patent is extended or adjusted under 35 U.S.C. 154(b) by 2920 days.

(21) Appl. No.: 10/572,776

(22) PCT Filed: Sep. 2, 2004

(86) PCT No.: PCT/IB2004/051729
§ 371 (c)(1),
(2), (4) Date: Mar. 21, 2006

(87) PCT Pub. No.: WO2005/030045
PCT Pub. Date: Apr. 7, 2005

(65) Prior Publication Data
US 2007/0049815 A1    Mar. 1, 2007

Related U.S. Application Data

(60) Provisional application No. 60/506,457, filed on Sep. 26, 2003.

(51) Int. Cl.
*A61B 5/05* (2006.01)
*A61B 6/00* (2006.01)
(Continued)

(52) U.S. Cl.
CPC ............... *A61B 6/56* (2013.01); *A61B 5/0002* (2013.01); *G06F 19/3418* (2013.01); *A61B 8/565* (2013.01)

(58) Field of Classification Search
CPC ....... A61B 5/0002; A61B 6/56; G06F 19/3418
USPC ............... 600/407; 709/200, 224, 217, 219; 382/128; 705/2
See application file for complete search history.

(56) References Cited

U.S. PATENT DOCUMENTS 5,839,442 A * 11/1998 Chiang et al. ............... 600/447
5,851,186 A    12/1998 Wood et al. ................ 600/437
(Continued)

FOREIGN PATENT DOCUMENTS

JP    2003093354 A    4/2003

OTHER PUBLICATIONS

Reponen, et al., "Initial Experience with a Wireless Personal Digital Assistant As a Teleradiology Terminal for Reporting Emergency Computerized Tomography Scans", Journ. Of Telemedicine & Telecare 2000, 6:45-49.

*Primary Examiner* — Baisakhi Roy

(57) ABSTRACT

A bi-directional communication system (12) is utilized for communications between a technician at an imaging workstation (18), from which imaging protocols can be conducted and at which diagnostic images can be displayed, and one or more hospital medical professionals, located at remote locations. The technician selects and addresses the proper medical professional by a use of an addressing means (50) at workstation (18). The technician selects images (42) to be sent to the selected medical professional. The images and medical professional's address are formatted (46) into wireless transmission format via transmitter/receiver (44) coupled to the workstation (18). A plurality of remote transmitters/receivers (62) receives wireless transmissions at remote locations. Each wireless transmission is examined (68) for a correct address and further converted (70) into an appropriate format for human-readable display. The selected medical professional reviews the images (42) and other information and releases the patient, who awaits the reviewing medical professional's response in the vicinity of the scanner (16).

20 Claims, 5 Drawing Sheets

(51) Int. Cl.
*A61B 5/00* (2006.01)
*G06F 19/00* (2011.01)
*A61B 8/00* (2006.01)

(56) References Cited

U.S. PATENT DOCUMENTS

| | | | |
|---|---|---|---|
| 6,112,234 A * | 8/2000 | Leiper | 709/219 |
| 6,440,072 B1 | 8/2002 | Schuman et al. | 600/437 |
| 6,475,146 B1 | 11/2002 | Frelburger et al. | 600/437 |
| 6,501,818 B1 | 12/2002 | Ali et al. | 378/4 |
| 6,656,118 B2 * | 12/2003 | Sharma et al. | 600/437 |
| 7,797,367 B1 * | 9/2010 | Gelvin et al. | 709/200 |
| 2002/0091659 A1 | 7/2002 | Beaulieu et al. | 706/62 |
| 2003/0179292 A1 | 9/2003 | Provost et al. | 348/143 |
| 2005/0049495 A1 * | 3/2005 | Sumanaweera et al. | 600/437 |
| 2005/0063575 A1 * | 3/2005 | Ma et al. | 382/128 |

* cited by examiner (Continuation)

ENABLEMENT OF QUICK REMOTE ACCESS TO CT SCANS TO IMPROVE WORKFLOW AND PATIENT THROUGHPUT

CROSS REFERENCE TO RELATED APPLICATIONS

This application claims the benefit of U.S. provisional application Ser. No. 60/506,457 filed Sep. 26, 2003, which is incorporated herein by reference.

DESCRIPTION

The present invention relates to the diagnostic imaging systems and methods. It finds particular application in conjunction with improving the throughput of CT scanners and other diagnostic equipment and will be described with particular reference thereto. However, it is to be appreciated that the invention will also find application in conjunction with improving medical processing efficiency, diagnostic efficiency, and the like.

Typically, in a CT scan, the patient is loaded into a patient support couch and taken into the CT scan room. A set of diagnostic images is generated by a CT scan technician from the exam room which is usually adjacent to the scan room. If there is any question whether the scan had the right contrast, covered the right region, or the like, it is necessary to page the medical specialist who can be in some other remote part of the hospital performing other duties. Depending on the size of the hospital, there could be a 10-15 minute wait for the paged medical specialist to terminate the duties being performed and reach a viewing terminal, review the images, and approve them. Interrupting a consultation with another patient or physician may not be appropriate. The patient is held in the scan room until the approval is made and the reviewing medical specialist authorizes patient's release.

Furthermore, in many CT scan protocols, the patient is injected with a contrast agent prior to imaging. During the delay, the contrast agent is being removed from the region of interest, e.g., by the patient's kidneys. If the delay was too long and a further set of images is required, the contrast agent concentration will have dropped below acceptable levels for the protocol. Re-injection of the contrast agent is a highly undesirable medical procedure. First, the contrast agent is often mildly toxic and overexposure can have negative physiological consequences. Second, gauging the amount of contrast agent to add by re-injection without overdosing the patient is difficult. The delay and re-injection creates concerns particularly with the pediatric patients who tend to be more sensitive to the contrast agents.

In addition, the healthcare system, and the diagnostic medical imaging as an integral part of it, is facing a challenging situation of shrinking budgets, increasing cost pressure, and growing demands to increase both the efficiency and quality of services. Professionalism and success are based on a strict approach to customer orientation and cost effectiveness.

Accordingly, there is a need to improve the workflow between the scan room personnel and the reviewing medical personnel to provide a speedy review of the scans for accuracy and completeness without burdening patients.

The present invention provides a new and improved apparatus and method which overcomes the above-referenced problems and others.

In accordance with one aspect of the present invention, an imaging communication system for communicating between an imaging workstation, from which imaging protocols can be conducted and at which diagnostic images can be displayed, and one or more medical professionals is disclosed. A means selects and addresses one or more medical professionals. A means selects electronic image representations to be sent to the one or more selected medical professionals. A means formats the at least one selected medical professional's address and the selected electronic image representations into a wireless transmission format. A plurality of remote receiving means receives wireless transmissions at remote locations. An address reading means is connected with each of the plurality of receiving means for examining each received wireless transmission for a corresponding preselected address. A video processing means is connected with each remote receiving means for, in response to the address reading means finding the corresponding preselected address in the received wireless communication, converting an electronic image portion of the received wireless transmission into an appropriate format for human-readable display.

In accordance with another aspect of the present invention, a method of imaging communications between an imaging workstation and one or more medical professionals is disclosed. An address of a medical professional and diagnostic images to be sent to the medical professional are selected. The medical professional's address and the images are formatted for wireless transmission. Wireless transmissions are received at remote locations. Each received wireless transmission is examined for a corresponding preselected address. After the corresponding preselected address is found in the received wireless communication, an electronic portion of the received wireless transmission is converted into an appropriate format for human-readable display.

One advantage of the present invention resides in a speedy review of scans for accuracy and completeness and timely release of patients from the scanning premises.

Another advantage resides in improved patient satisfaction.

Another advantage of the present invention resides in the optimization of communications between the imaging technician and the reviewing medical personnel.

Other advantages include that the scan technician and the medical personnel can communicate and react quickly in the emergency situations, costs and response times are reduced, the quality of the outcome for the patients increases, therapeutic decisions are accelerated (e.g., real-time scanning), and unnecessary waiting times for current patents and those awaiting services are avoided.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not be construed as limiting the invention.

Figure 1:
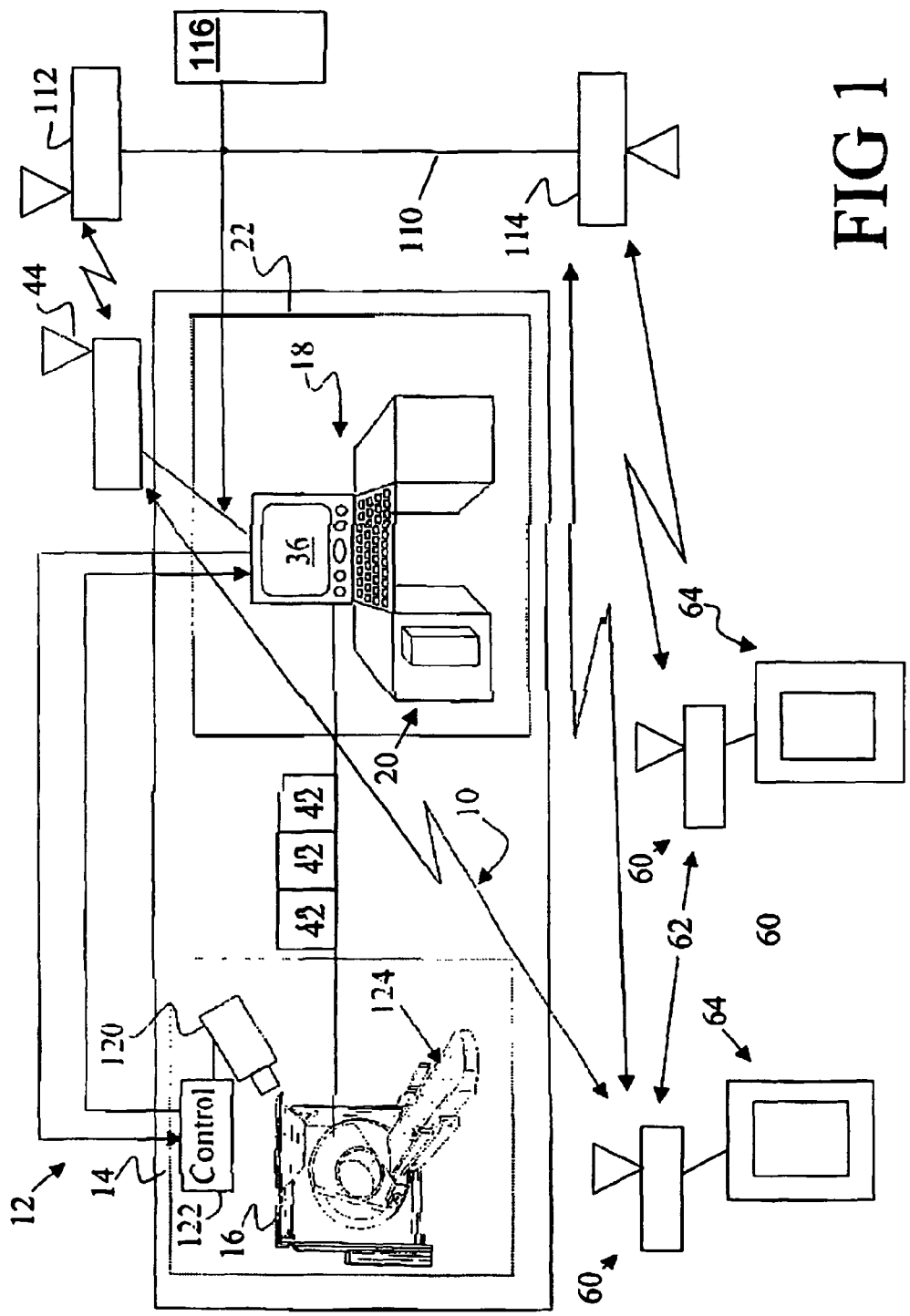
FIG. 1 is a diagrammatic illustration of the two-directional communication system.

With reference to FIG. 1, a two-way communications link 10 is established between a medical professional such as radiologist and imaging technician in a multi-media bi-directional communication system 12. The radiologist and imaging technician can communicate verbally, the radiologist can dictate notes, the patient chart or records can be sent as well as real-time images of the patient. Of course, it is contemplated that the communications can take place between the imaging technicians and other medical professionals such as physicians, cardiologists, other imaging technicians, and the like.

Typically, a patient is taken into a scanning room 14, which contains scanning apparatus 16. The imaging technician performs a scan using a workstation 18 loaded with software 20 and located in a technician's room 22.

Figure 2:
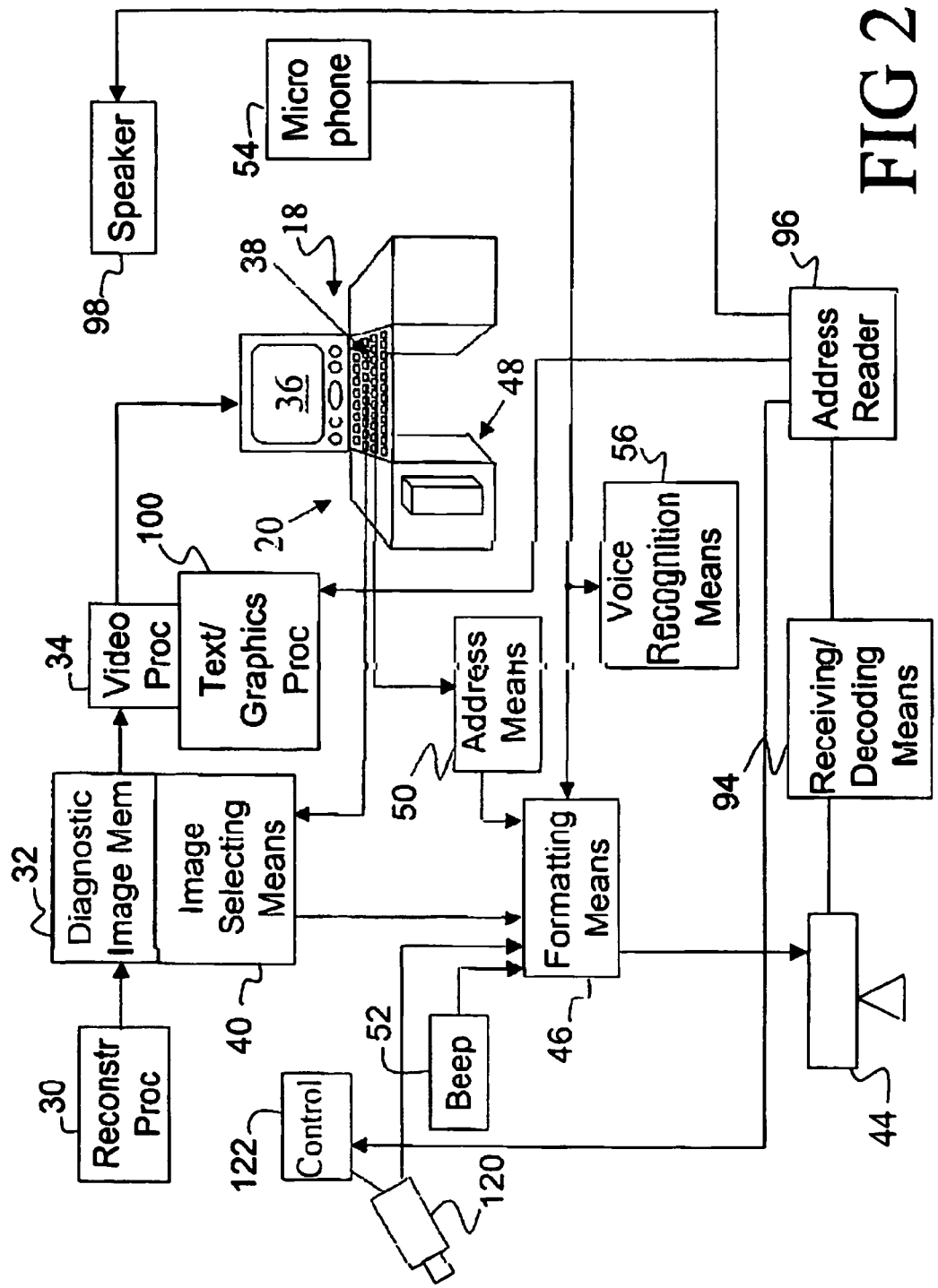
FIG. 2 is a diagrammatic illustration of a part of the two-directional communication system that is positioned in the vicinity of a scanner.

With reference to FIG. 2, diagnostic data from the scanner 16 is reconstructed by a reconstruction processor 30 into electronic image representations which are stored in a diagnostic image memory 32. The reconstruction processor 30 may be incorporated into the workstation 18, the scanner 16, or may be a shared resource among a plurality of scanners and workstations. The diagnostic image memory 32 preferably stores a three-dimensional image representation of an examined region of the subject. A video processor 34 converts selected portions of the three-dimensional image representation into appropriate format for display on a video monitor 36. An operator input device, such as a keyboard 38 controls a diagnostic image selecting means 40, which selects orthogonal slice images, oblique slices images, projections, three-dimensional renderings, or other portions of the three-dimensional diagnostic image representation.

With reference again to FIG. 1 and continuing reference to FIG. 2, the imaging technician views reconstructed images 42 on the monitor 36 and sends them to the radiologist via transmitting/receiving means or transmitter/receiver 44 coupled to workstation hardware 48. More specifically, the technician at the workstation 18 uses the keyboard 38 to access radiologist's address means 50 and the image selecting means 40 that send the selected address and the selected image representations to a formatting means or software 46, which formats the images and the selected address into appropriate format for wireless transmission by the transmitting/receiving means 44. Optionally, the formatting means 46 may also incorporate electronic signals, which will cause a beep or other attention getter 52 when the formatted message is read. Optionally, a microphone 54 is disposed adjacent the workstation 18 so that the technician can also generate voice instructions, which are also formatted into the message, either as audio signals or as text signals, after being converted by voice recognition software 56.

With continuing reference to FIG. 1, the radiologist reviews the images 42 using a personal digital assistant device (PDA) or a tablet PC or other portable hardware unit 60, which has an associated remote transmitting/receiving means or transmitter/receiver 62. The radiologist communicates back to the workstation 18 that the patient can be released or requests more information. Software 64, loaded into the portable hardware unit 60, is compatible with the software 20 loaded into technician's workstation 18.

Figure 3:
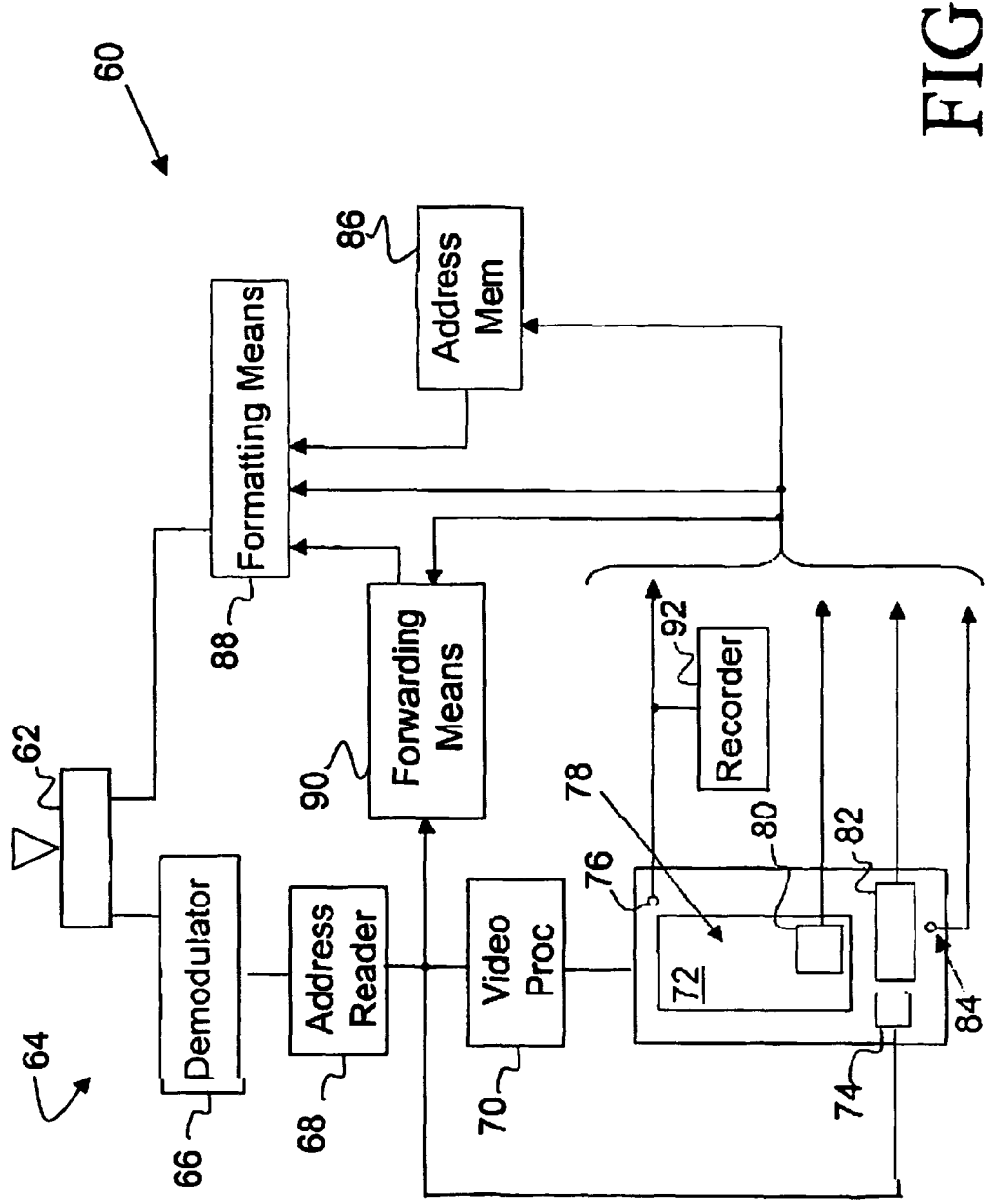
FIG. 3 is a diagrammatic illustration of a part of the two-directional communication system that is positioned in one or more remote locations.

With reference to FIG. 3, the software 64 includes a receiver or demodulator 66 which makes any necessary formatting adjustments of a received wireless message. An address reader 68 reads the address of each received message. If a received message is addressed to the receiving portable unit 60, image representations in the message are passed to a video processor 70, which formats the representations into appropriate form for display on a video display or monitor 72. Voice signals, a beep, or other audio signals are passed to a speaker 74. To reply to the workstation 18, the portable unit includes a microphone 76 into which the diagnostician can send verbal instructions to the operator at the workstation 18 to release the patient, conduct additional scans, reduce some of the scans with different parameters, or the like. In some situations, such as when the diagnostician is consulting with a patient or other physicians, a verbal reply may be inappropriate. To this end, the video display 72 includes a touch screen 78, either incorporated into the monitor 72 itself or through an overlay, laser grid, or the like. Various touch screen displays are contemplated, such as an "accept" button 80. Optionally, the portable unit 60 may also include a keypad 82 or a joystick 84. The control signals are used to select an address of the workstation or other remote unit from an address memory 86. A formatting means or software 88 formats the instruction signals and the address into appropriate format for transmission by the transmitter/receiver 62.

Optionally, the radiologist may chose to contact another remote unit to consult with that radiologist. One of the input means is used to select the address of that radiologist's remote unit from the address memory 86 and controls a forwarding means or software 90, which forwards all or selected ones of the received images along with the conferring radiologist's address to the formatting means or software 88. Optionally, the microphone 76 is connected with a recorder 92 such that the radiologist can record notes for later replay or transcription.

With reference again to FIG. 2, the further instructions to the technician at the workstation 18 are received at the transmitter/receiver 44. A receiving and decoding means 94, along with receive portions of the transmitter/receiver 44 decodes the received message into appropriate format for further analysis and utilization by the software 20. An address reader 96 determines whether the workstation 18 is the addressed recipient of a received message. If so, it forwards audio portions of the received message to a speaker 98. Text or the input to pushbuttons on the touch screen are forwarded to a text or graphics processor 100 which causes the video processor 34 to superimpose appropriate text or icon messages on the video display 36.

With reference again to FIG. 1, the two-way communication can be established over an existing or added hospital network 110. The workstation 18 may be hardwired to the network or may communicate with it by way of a wireless interface 44-112. The hospital network includes a plurality of wireless interfaces 114 in different rooms of the hospital that can communicate with the wireless receiving/transmitting units 62 of the portable units 60. In this manner, the technician at the workstation 18 can communicate with radiologists at remote locations around the hospital. As yet another alternative, the workstation 18 or the hospital network can be connected via land lines or cell phone connections to a cell phone tower 116. The transmitter/receiver unit 62 of the portable units 60 can be configured to receive messages wirelessly over cell phone lines. This enables the images to be forwarded to radiologists who are located in a region of the hospital where there are no wireless interfaces or at locations remote from the hospital.

With continuing reference to FIG. 1 and reference again to FIG. 2, a camera 120 is optionally mounted in the scan room to view the patient being scanned. The exterior appearance of a patient can be of particular significance when diagnosing trauma victims. The camera is connected with an electromechanical controller 122 which can be used to change the field of view of the camera by zooming its lens, tipping the camera to different angles, and the like. The electromechanical controller 122, preferably, can adjust the focus of the camera 120. If the camera 120 is a still camera rather than a video camera, the electromechanical controller 122 further triggers the taking of still pictures. Optionally, the camera 120 is brought under the control of the diagnosing radiologist at the remote location. Camera control signals from the remote location are forwarded by the address reader 96 to the electromechanical controller 122 to make the appropriate camera adjustments. The output of the camera is connected to the formatting means 46 to format the electronic optical images from the camera into messages addressed to the controlling remote location.

Figure 4:
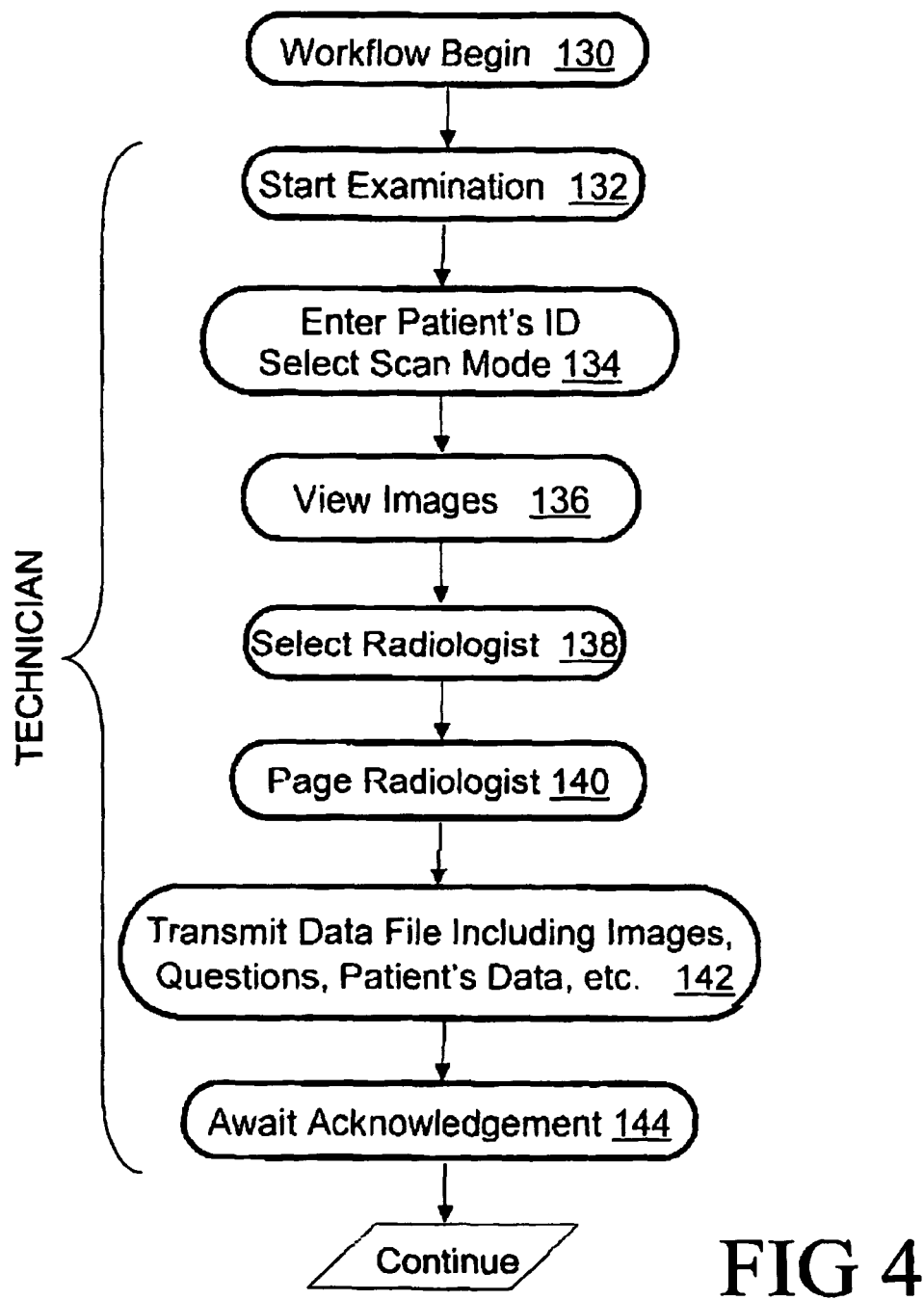
FIG. 4 is a block-diagram of a work-flow between an imaging technician and a reviewing medical professional.
Figure 4:
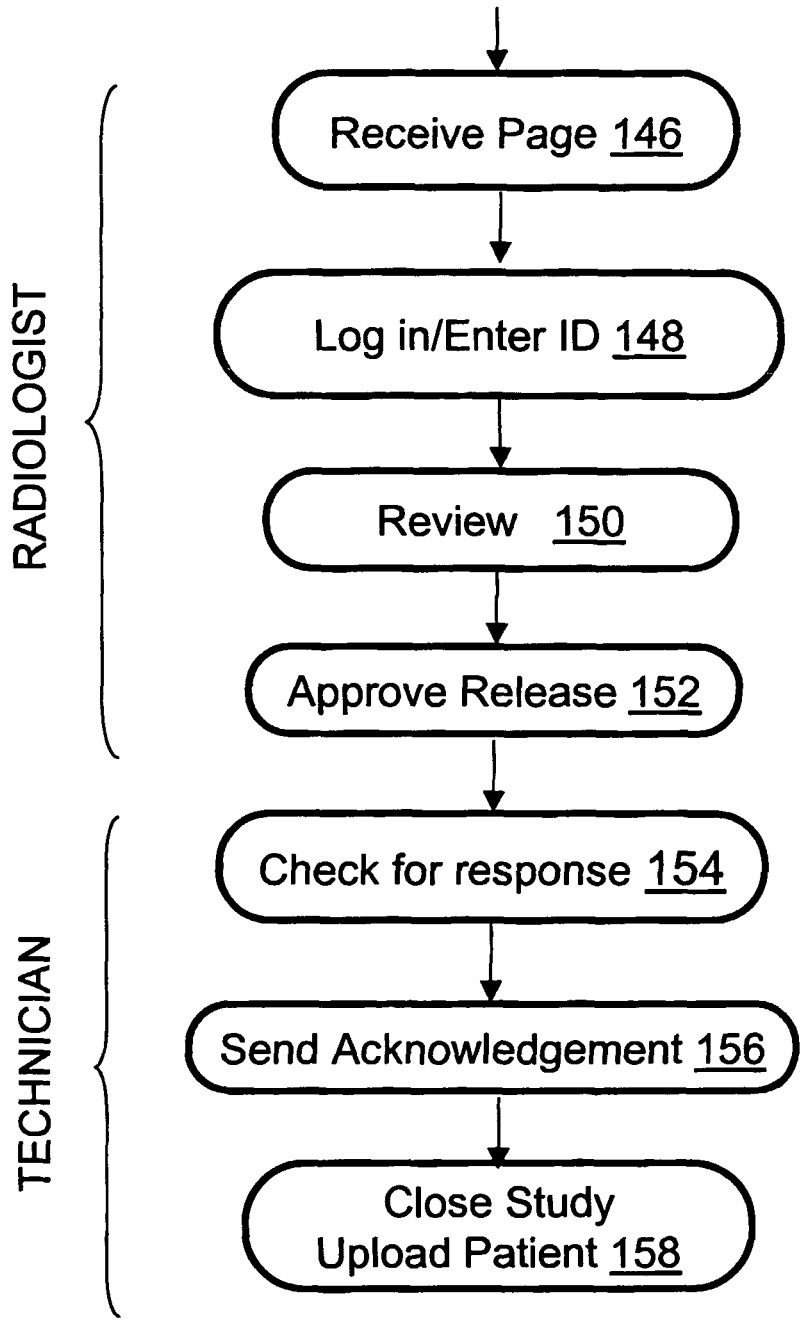

With reference to FIG. 4, a workflow begins 130 after the patient is injected with a contrast agent and taken into the scanning room 14. The technician starts an examination 132 by entering the patient ID and selecting a scan protocol 134. After the scans are obtained, technician views the scans 136. The technician selects a correct radiologist or physician in charge 138 and sends a page 140. At the same time, the technician transmits images 142 via e-mail or the wireless communications means 44, 62 and awaits a predetermined time to receive an automatically generated acknowledgement 144.

With continuing reference to FIG. 4, the radiologist receives the page 146 and executes a login 148 to access the arrived patient images. The software means 64 matches the radiologist ID code and the patient's code to ensure that the correct radiologist is reviewing the correct patient's data. If the radiologist ID code is accepted, the software authorizes the radiologist to proceed. The software means 64 generates an automatic "ok" message back to the technician. If the radiologist ID code does not match the patient's code, the software declines access and generates automatic "decline" message that is sent back to the technician.

The radiologist reviews the scans 150 for correctness, completeness, proper contrast, and other relevant criteria. The radiologist may approve a release of the patient 152, request additional scans, request repetition of selected scans, or request more information such as patient's files or an exterior image of the patient, which is particularly advantageous in the trauma cases. The exterior image of the patient can be taken with a hand-held digital camera or with a real-time video camera in the exam room 14 or on the scanning apparatus 16. The radiologist can control the live video from the tablet computer or the like to control zoom, field of view, and other.

The technician checks for the radiologist response 154. After technician receives radiologist's response, he sends an acknowledgement that it is received 156. Accordingly, technician closes the study and releases the patient, repeats all or part of the study, or sends more data 158 to the radiologist.

As a further enhancement, two or more radiologists or physicians can view the images and communicate with one another. For example, a first radiologist can send images to a second radiologist for consultation that can be carried on verbally or by typing text directly between two radiologists.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

Having thus described the preferred embodiments, the invention is now claimed to be:

1. An imaging communication system for communicating between an imaging workstation, from which imaging protocols are conducted and at which diagnostic images are displayed, and one or more medical professionals, the system comprising:

the workstation including:

an input device by which a user selects and addresses one or more medical professionals and selects diagnostic image representations to be sent to the one or more selected medical professionals;

a unit which formats the at least one selected medical professional address and the selected diagnostic image representations into a wireless transmission format and wirelessly transmits the selected electronic image representation with the selected medical professional address;

a plurality of remote units, each remote unit including:

a receiver which receives wireless transmissions from workstations and from other remote units;

an address reader connected with the receiver which address reader examines each received wireless transmission for a corresponding preselected address;

a video processor connected with the receiver to, in response to the address reader finding the corresponding preselected address in the received wireless communication, convert a diagnostic image portion of the received wireless transmission into an appropriate format for human-readable display; and a display device on which the diagnostic image is displayed in human-readable format.

2. The system as set forth in claim 1, the remote units are portable units and each communicates wirelessly with the workstation and the other portable units and each portable unit further includes:

an input unit through which the medical professional associated with the portable unit inputs (1) address of other portable units, (2) instructions to transfer the diagnostic image to an addressed portable unit, and (3) at least one of voice and text communications such that the medical professional associated with the portable unit can confer with medical professionals associated with other portable units and/or the workstation about the diagnostic image.

3. The system as set forth in claim 2, wherein the portable units include at least one of notebook computers and tablet personal computers which have sufficient resolution that the associated medical professional can determine if the diagnostic image is satisfactory for diagnostic purposes.

4. The system as set forth in claim 2, further including:

a diagnostic scanner disposed in a scan room adjacent the imaging workstation, the imaging workstation communicating the imaging protocols to the diagnostic scanner to control the diagnostic scanner during an imaging process of a subject in the diagnostic scanner to generate the diagnostic image.

5. The system as set forth in claim 4, wherein the imaging workstation addresses and communicates the diagnostic images of the subject in the diagnostic scanner to the portable unit associated with a one of the medical professionals responsible for reviewing the diagnostic images of the subject and the portable unit input unit further includes:

at least one of a microphone, a touch screen, a keypad, and a joystick or mouse by which the one of the medical professionals wirelessly sends communications to an operator of the imaging workstation.

6. The system as set forth in claim 5, wherein the communications from the medical professionals to the operator include:

messages approving the diagnostic images and authorizing release of the subject; and messages requesting that the operator control the diagnostic scanner to perform another imaging process with another protocol.

7. The system as set forth in claim 4, wherein the portable unit input unit includes a microphone and formatting electronics which format audio information from the microphone into an appropriate format for wireless transmission such that the one of the medical professionals associated with the portable unit that received the diagnostic images can forward the diagnostic images to other medical professionals and verbally discuss the diagnostic images with the other medical professional.

8. The system as set forth in claim 2, wherein the workstation further includes:
a receiver which receives wireless communications from the portable units;
an address reader which reads an address portion of the received wireless communications and determines whether the received address portions match a preselected workstation address; and
a converting unit which converts an input information portion of the received wireless communication whose corresponding address portion matches the preselected workstation address into at least one of a human-readable and hearable format.

9. The system as set forth in claim 1, wherein the formatting unit is connected with a hospital based network, which includes wireless transmission units.

10. The system as set forth in claim 1, further including:
a diagnostic scanner which conducts a diagnostic scan of a patient positioned in the diagnostic scanner under control of the workstation to generate diagnostic image information;
a reconstruction processor which reconstructs the generated diagnostic information into diagnostic images.

11. The system as set forth in claim 1, wherein the patient has been injected with a contrast agent and the workstation and the remote units further include:
transmitters and receivers for at least one of voice and text communications which wirelessly transmit voice and/or text communications between the workstation and the remote units such that while holding the patient in the diagnostic scanner, the diagnostic images are transferred to one of the remote units and displayed to a medical professional; and
such that after analysis of the human-readable display, the transmitters and receivers wirelessly transmit voice and/or text instructions to the workstation to one of: (1) release the patient and (2) conduct further diagnostic scans while the contrast agent is still in the patient.

12. The system as set forth in claim 1, further including:
a video camera which optically images the patient in the diagnostic scanner to generate electronic optical images of the patient, the workstation formatting unit formats the optical video images and a selected medical professional's address into format for wireless transmission to the remote unit associated with the selected medical professional.

13. The system as set forth in claim 12, wherein the remote units further include:
an input device which wirelessly controls a field of view of the video camera which generates the optical video images.

14. The system as set forth in claim 1, further including:
a patient records database;
a wireless transmitter connected with the database which, in response to the instructions from one of the remote units, wirelessly transmits patient records to the one remote unit.

15. The system as set forth in claim 1, wherein the remote unit includes a wireless transmitter and the workstation includes a wireless receiver such that after reviewing the diagnostic images an approval of the diagnostic images is wirelessly sent to the workstation and the patient in the scanner is released.

16. The system as set forth in claim 1, wherein the remote unit includes a wireless transmitter and the workstation includes a wireless receiver such that after analyzing the diagnostic image on the remote unit display device, instructions are wirelessly sent to the workstation to control the diagnostic scanner to generate additional diagnostic images of the patient.

17. An imaging communication system for communicating between an imaging workstation, from which imaging protocols can be conducted and at which diagnostic images can be displayed, and one or more medical professionals, the workstation being disposed adjacent a scan room, the system comprising:
a means for selecting and addressing one or more medical professionals;
a means for selecting electronic image representations to be sent to the one or more selected medical professionals;
a means for formatting the at least one selected medical professional address and the selected electronic image representations into a wireless transmission format; and
a diagnostic scanner disposed in the scan room;
a patient support for supporting a patient in the diagnostic scanner;
an electronic camera disposed in the scan room to view the patient on the patient support, the electronic camera being connected with the formatting means to format electronic pictures from the electronic camera for wireless communication to a selected portable unit;
a plurality of portable units, each unit including:
a monitor means for generating the human-readable display,
a remote receiving means for receiving wireless transmissions at remote locations,
an address reading means connected with the receiving means for examining each received wireless transmission for a corresponding preselected address, and
a video processing means connected with the remote receiving means for, in response to the address reading means finding the corresponding preselected address in the received wireless communication, converting an electronic image portion of the received wireless transmission into an appropriate format for human-readable display.

18. The system as set forth in claim 17, further including:
an electromechanical control means for adjusting at least one of a field of view, focus, and direction of the electronic camera, the electromechanical control means being connected with a receiving means and a workstation address recognition means to receive control signals originating with the input means of the portable unit.

19. The system as set forth in claim 17, wherein the diagnostic scanner includes a diagnostic scanner and the image representations include diagnostic images of the patient, such that the diagnostic images and the electronic pictures are both communicated to the selected medical professionals and wherein the portable units further include:
    an input means for selecting one or more of other ones of the medical professionals and an operator of the workstation and communicating the diagnostic images and/or the electronic pictures to selected other medical professionals and for sending messages to the selected other medical professionals and the operator such that selected medical professionals can confer on the diagnostic images and/or the electronic pictures and provide instructions to the operator to control the diagnostic scanner to generate additional diagnostic images.

20. An imaging scanner communication system comprising:
    a diagnostic scanner disposed in a hospital which generates diagnostic images of a patient disposed in the diagnostic scanner;
    an optical camera disposed adjacent the diagnostic scanner to generate electronic optical images of the patient disposed in the diagnostic scanner;
    a workstation which facilitates wireless data transfer between diagnostic scanner operating personnel and one or more hospital radiologists moving around the hospital and remote from the workstation, the workstation receiving the diagnostic images from the diagnostic scanner and the optical images in electronic format and formatting the images for wireless transmission;
    a wireless communication unit coupled to the workstation which wirelessly transmits patient information and the diagnostic images and the optical images to a selected one of the hospital radiologists; and
    a plurality of portable units each carried by one of the hospital radiologists, each portable unit including:
        a wireless communications unit which each portable unit receives the patient information, diagnostic images and optical images wirelessly transmitted from the workstation and addressed to it and wirelessly transmits instructions input on an input unit to the workstation, the instructions including instructions to the diagnostic scanner operating personnel regarding the patient in the scanner including instructions for acceptance of the diagnostic images and instructions to re-scan the patient in the diagnostic scanner, each portable unit further including a display on which the diagnostic and optical images are displayed.

* * * * *